United States Patent [19]

Lam et al.

[11] Patent Number: 4,871,350

[45] Date of Patent: Oct. 3, 1989

[54] METHODS AND COMPOSITIONS FOR PREVENTING SECONDARY CATARACTS

[75] Inventors: Dominic M-K. Lam; Peter J. Kelleher, both of The Woodlands, Tex.

[73] Assignee: Baylor College of Medicine, Houston, Tex.

[21] Appl. No.: 204,168

[22] Filed: Jun. 8, 1988

Related U.S. Application Data

[63] Continuation-in-part of Ser. No. 927,318, Nov. 4, 1986, abandoned.

[51] Int. Cl.$^4$ ............................................. A61M 31/06
[52] U.S. Cl. ....................................... 604/49; 514/912
[58] Field of Search .............................. 530/387–389, 530/849; 514/912–915; 604/20, 49, 172; 424/85; 436/547–548

[56] References Cited

U.S. PATENT DOCUMENTS

| | | | |
|---|---|---|---|
| 4,307,082 | 12/1981 | Rosenberg | 424/115 |
| 4,340,535 | 7/1982 | Voisin et al. | 435/172.2 |
| 4,342,828 | 8/1982 | Takaku et al. | 424/99 |
| 4,349,528 | 9/1982 | Koprowski et al. | 424/85 |
| 4,363,758 | 12/1982 | Musuho et al. | 435/172.2 |
| 4,379,145 | 4/1983 | Musuho et al. | 435/172.2 |
| 4,432,751 | 2/1984 | Emery et al. | 604/49 |
| 4,657,930 | 4/1987 | Emery et al. | 514/912 |
| 4,661,347 | 4/1987 | Muller-Eberhard | 424/85 |
| 4,665,089 | 5/1987 | Siezen et al. | 514/912 |
| 4,778,815 | 10/1988 | Cash | 514/912 |
| 4,778,828 | 10/1988 | Palmai et al. | 514/912 |
| 4,797,422 | 1/1989 | Testa | 514/912 |
| 4,814,275 | 3/1989 | Durda et al. | 435/172.2 |
| 4,826,872 | 5/1989 | Terao et al. | 514/474 |

FOREIGN PATENT DOCUMENTS

1178206  11/1984  Canada .................................. 514/912

OTHER PUBLICATIONS

Blythman et al., "Immunotoxins: Hybrid Molecules of Monsclonal Antibodies and a Toxin Subunit Specifically Kill Tumour Cells", Nature, vol. 290, pp. 145–146, 1981.
Youle, "Antibody Linked to Ricin is a Potent Al-1-Type-Specific Toxin", Proc. Natl. Sci., USA, vol. 77, No. 9, pp. 5483–5486, 9/80.
Gilliland et al., "Chimeric Toxins", Proc. Natl. Acad. Sci. USA, vol. 75, No. 11, pp. 5319–5323, Nov. 1978.
Szoka et al., "Procedure for Preparation of Lipisones", Proc. Natl. Acad. Sci. USA, vol. 75, No. 9, pp. 4194–4198, Sep. '78.
Campbell, "Monoclonal Antibody Technology", *Laboratory Techniques in Biochemistry and Molecular Biology,* vol. 13, pp. 16–25, 1986.
Olsnes et al., "Diff. Biol. Properties of the 2 Constituent Peptide Chains of Recin . . .", Biochemistry, vol. 12, No. 16, 1973, pp. 3121–3126.
Mussuho et al., "Prep. of a Hybrid of Fragment Fab' of Antibody and Fragment A of Diptheria Toxin and Its Cytotoxicity", Biochemical and Biophysical Research Communications, vol. 90, No. 1, 1979, pp. 320–326.
Heath et al., "Anti-Body Targeted Liposomes", Proc. Natl. Sci. USA, vol. 80, pp. 1377–1381, 3/83.
Russell et al., "The Development of a Monosclonal Antibody to a Human Gamma Crystallin", Current Eye Research, vol. 3, No. 11, pp. 1329–1335, 1984.
Kincses et al., "Experimental Production of Antibodies Against Cataractous Human Lens", Acta. Medica. Acad. Sci., vol. 31(1–2), pp. 9–13, 1974.
Nissen et al., "Antibodies to Lens Antigen in Cataract and After Cataract Surgery", British J. of Ophthalmology, vol. 65, pp. 63–66, 1981.
Cole et al., "Enzymatic Zonulolysis and Cryoextraction of Cataracts", International Surgery, vol. 50, No. 3, pp. 242–244, Sep. 1968.

*Primary Examiner*—C. Fred Rosenbaum
*Assistant Examiner*—Sharon Rose
*Attorney, Agent, or Firm*—Barbara Rae-Venter; Bertram I. Rowland

[57] ABSTRACT

Novel methods and compositions are provided for preventing secondary cataracts. A cytotoxic agent is employed which is introduced into the anterior chamber of the eye to inhibit proliferation of remnant lens epithelial cells after extracapsular cataract extraction. Desirably a non-cytotoxic agent cross-reactive with the cytotoxic agent is introduced prior to introduction of the cytotoxic agent. The agents can be provided as kits.

4 Claims, No Drawings

METHODS AND COMPOSITIONS FOR PREVENTING SECONDARY CATARACTS

This application is a continuation-in-part of application Ser. No. 927,318, filed Nov. 4, 1986, now abandoned, which disclosure is incorporated herein by reference.

INTRODUCTION

1. Technical Field

The field concerns methods and compositions for inhibiting secondary cataracts using cytotoxic compositions which react specifically with lens epithelial cells.

2. Background

Extracapsular cataract extraction is a desirable method for removing cataracts due to a lower incidence of post-operative complications in terms of cystoid macular edema and possible retinal detachment with this technique. The availability of an improved extracapsular extraction technique such as phacoemulsification and the requirement of an intact posterior lens capsule for implantation of a wide variety of intraocular lenses has further supported extracapsular cataract extraction use. However, this surgical method is accompanied by a significant incidence of posterior lens capsule opacification, which may require additional surgical procedures (posterior capsulotomy or repolishing of the posterior lens capsule) to obtain good vision.

The pathogenesis of posterior lens capsule opacification after extracapsular cataract extraction is reported to be due to proliferation of remnant lens epithelial cells on the posterior lens capsule to form abortive lens "fibers" and "bladder" cells (i.e., Elschnig's pearls). Various techniques have been reported to inhibit this secondary cataract formation or posterior lens capsule opacification. Roy et al., *Contact and Intraocular Lens Medical Journal* (1979) 5:175–178 reported the use of vincristine and vinblastine. Radiation has also been tried and was reported to be promising. Methotrexate and retinoic acid have been reported for instillation in the anterior chamber of the eye to prevent posterior lens capsule opacification. These methods are relatively non-specific and can damage other cells in addition to the lens epithelial cells.

It would be of interest to develop substantially specific methods for preventing secondary cataract formation or posterior lens capsule opacification thereby avoiding potential side effects due to the use of cytotoxic agents. The unique anatomical location of the various cells types during cataract surgery makes possible the use of cytotoxic agents which are substantially specific for epithelial cells present in the anterior chamber of the eye. The method is preferably used in combination with pretreatment with a noncytotoxic agent having the same specificity for lens epithelial cells as the cytotoxic agent.

RELEVANT LITERATURE

Production of monoclonal antibodies has been described. See, for example, *Monoclonal Antibodies*, eds. Roger H. Kennett, Thomas J. McKearn, Kathleen B. Bechtol, Plenum Press, New York, 1980; *Nature* (1975) 256:495–497; U.S. Pat. Nos. 4,271,145; 4,196,265; 4,172,124; 4,195,125; 4,262,090; and 4,294,927. See also, U.S. Pat. No. 4,432,751, which discloses the combination of monoclonal antibodies and complement for preventing secondary cataracts.

SUMMARY OF THE INVENTION

Methods and compositions are provided for inhibiting posterior lens capsule opacification after extracapsular cataract extraction. The methods involve using cytotoxic agents specific for epithelial cells and introducing them into the anterior chamber of the eye concurrently with or subsequent to the extracapsular cataract extraction. Of particular interest is introducing non-cytotoxic agents into the anterior chamber prior to the introduction of the cytotoxic agents, where the non-cytotoxic and cytotoxic agents have substantially the same binding affinity for epithelial cells. The method is effective in preventing opacification of the posterior lens capsule.

DESCRIPTION OF THE SPECIFIC EMBODIMENTS

Methods and compositions are provided for inhibiting proliferation of remnant lens epithelial cells after extracapsular extraction. The method comprises introducing into the anterior chamber of the eye cytotoxic agents specific for epithelial cells, so as to substantially inhibit the proliferation of the lens epithelial cells. The cytotoxic agents are substantially specific for the lens epithelial cells and have low or no cross-reactivity with other cells found in the anterior chamber, such as fibroblasts, melanocytes, corneal endothelial cells, etc., desirably also other epithelial cells, e.g., corneal epithelial cells. Preferably, prior to introduction of the cytotoxic agent and prior to the extracapsular cataract extraction, a non-cytotoxic agent is introduced into the anterior chamber, where the non-cytotoxic agent is cross-reactive with or has substantially the same binding specificity as the cytotoxic agent, so as to bind to any cells in the anterior chamber which are in contact with the anterior chamber having homologous determinant or antigenic sites.

The cytotoxic agent is a conjugate of a protein macromolecule capable of binding substantially specifically to epithelial cells, particularly lens epithelial cells, as compared to other cells which may be present in or in contact with the anterior chamber of the eye. For the most part, cytotoxic compositions will be conjugates of a monoclonal antibody or its equivalent with a cytotoxic agent. The monoclonal antibody may be produced as a result of hybridoma formation and expression by the hybridoma, whether in culture or present as ascites, a monoclonal antibody fragment, such as Fab, F(ab')$_2$, Fv, a recombinant variable region, a T-cell receptor, or the like. The monoclonal antibodies and receptors may be any mammalian species, including murine, rabbit, human or the like, or combinations thereof, such as chimeric antibodies, having a human constant region and a mouse or other mammalian source variable region. The antibodies may be any class or subclass, such as IgA, IgD, IgG, IgM, and may include IgG$_1$, 2a, 2b, or 3 or the human equivalents thereof.

The methods for preparing the monoclonal antibodies are well established as evidenced by the numerous references described above. An animal is hyperimmunized with a suitable immunogen, with or without addition of adjuvant. Various epithelial cells may be used as the immunogen, particularly human epithelial cells, including tumor cells originating from epithelial cells, for example HeLa cells, although other species may find use, e.g., primates. Whole cells are preferred, however homogenates, membrane fragments or the like, can be used. The source of the cells includes cells in tissue culture, biopsy specimens, and the like. Antibody-producing cells such as spleen cells or lymphocytes from the immunized animal are removed and immortalized.

To identify hybridomas of interest, antibodies secreted by the immortalized cells are screened to identify the clones that secrete antibodies of the desired specificity. Screening of the hybridoma clones may be by binding to epithelial cells, particularly lens epithelial cells, using an ELISA assay. Other screening methods include radioimmunoassay and immunohistochemical staining of cryostat sections of ocular tissue. Furthermore, the resulting monoclonal antibodies may be isolated and modified by truncating the constant region by various peptidase digestions. The monoclonal antibodies may be reduced to provide for Fab fragments with available mercaptan sites for conjugation to other compositions. T-cell receptors may be obtained as described in WO85/03947.

The binding compositions having specificity for epithelial cells, may be joined to a wide variety of toxic agents which may be derived from microorganism or plant sources. Of particular interest are the toxic subunits of naturally occurring toxins, such as ricin, abrin, diphtheria toxin, etc. See for example Oeltmann and Heath, *J. Biol. Chem.* (1979) 254:1022–1027; Yule and Neville Jr., *Proc. Natl. Acad. Sci. USA* (1980) 77:5483–5486; Gilliland et al., *Proc. Natl. Acad. Sci. USA* (1978) 75:5319–5323; U.S. Pat. No. 4,379,145; GB2034324 and Masuho et al., *Biochem. Biophys. Res. Comun.* (1979) 90:320–326; and Blythman, *Nature* (1981) 290:145, the relevant disclosures of which are incorporated herein by reference.

Illustrative toxin A-chains or similarly effective moieties include diphtheria toxin A-chains, enzymically active proteolytic fragments from *Pseudomonas aeruginosa* exotoxin-A, ricin toxin A-chain, abrin A-chain, modeccin A-chain, and proteins found in various plants having similar activity, such as the plants e.g., *Gelonium multiflorum, Phytolacca americana, Croton tiglium, Jatropha curcas, Momordic charantia,* and wheat germ. Of particular interest is the toxin saporin from *Saponaria officinalis* (Thorpe et al., *J. Natl. Cancer Inst.* (1985) 75:151). Also, mutant species of the toxins of the species may be used, such as CRM45 (Boquet et al., *Proc. Natl. Acad. Sci. USA* (1976) 73:4449–4453).

The toxic agents and moiety providing for binding to the epithelial cells may be linked, usually by a bond which is cleavable cytoplasmically. Convenient linkages include disulfide, particularly where the toxic agent has an intrinsic sulfur, or other links, such as peptide links, urea links, thioethers, imines, amides, imides, amidines, etc. Functional groups which may find employment include carboxylic acid groups, amino groups, imines, aldehydes, isocyanates, mercaptans, olefins, or the like. In addition, more complex linking groups can be employed, where a group may be bound to one of the moieties in the conjugate to provide for convenient linkage to an intrinsic group of the other moiety. For example, the N-hydroxysuccinimide ester of m-maleimidoylbenzoic acid may be employed to prepare an amide of the toxin, which may then be linked through an available sulfur atom on the monoclonal antibody to provide a thioether.

Exemplary cytotoxic agents may have the following formula:

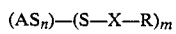

$(AS_n)—(S—X—R)_m$ wherein:

$AS_n$ indicates the toxic agent having one or more sulfur groups as part of the agent; n is 1 to the number of sulfur groups present in the toxic agent which are present as available mercaptide groups, generally being up to about 4; R is a monoclonal antibody receptor or derivative thereof; and m is 1 up to n, usually being from 1 to 2; and X is a linking group and may be a bond or a group of from about 1 to 20, usually 1 to 12 atoms other than hydrogen, which include carbon, nitrogen, oxygen and sulfur. Sulfur will normally be bonded to carbon, particularly aliphatically saturated. X may be aliphatic, alicyclic, aromatic, heterocyclic or combinations thereof, generally having from 0 to 6, more usually from about 0 to 4, preferably about 1 to 4 heteroatoms, wherein oxygen and sulfur are present as oxo or non-oxo-carbonyl or the thio analogs thereof, or ether (including thioether), and nitrogen is present as amino or amido. For the most part the heteroatoms will be bonded solely to carbon.

Illustrative groups linking the disulfide include aminoethylene 3-propanyl methylene carbonyl, α-succinimidyl, 3-propylenethiocarbonyl. The groups which may be used are for the most part conventional groups providing for a disulfide linkage. The disulfide compound is one which is capable of reacting with the cell-specific ligand, whereby a mercaptide group may be displaced from the disulfide, resulting in a new disulfide linkage between the toxic agent and the ligand.

For the most part, the linkages will be aliphatic of from about 1 to 6 carbon atoms, providing for an amide bond to the receptor, although this is primarily a matter of convenience, not necessary to the operability of the subject compositions.

Other toxic agents may also be used, such as bismuth non-diffusively linked to the monoclonal antibodies or receptors as described by Waldman, *J. Amer. Med. Assoc.*

Alternatively, liposomes may be linked to the monoclonal antibodies or receptors, where the liposomes contain various cytotoxic agents, such as methotrexate, 5-fluorouracil, any of the above toxins, or the like. See, for example, Szoka and Papahadjopoulos, *Proc. Natl. Acad. Sci. USA* (1978) 75:4194–4198 and Szoka et al., *Biochem. et Biophys. Acta.* (1980) 601:559–571 for the preparation of liposomes, which disclosures are incorporated herein by reference. Linking of antibodies to the liposome has been amply described in the literature, see for example Heath et al., *Proc. Natl. Acad. Sci. USA* (1983) 80:1377–1381 and Leserman *et al., Nature* (1981) 293:226–228, whose disclosures are incorporated herein by reference.

Other cytotoxic agents conjugated to the binding moiety may also be employed in conjunction with the subject process of this invention. The conjugate will be sufficient to provide the cytotoxic effect without the addition of ancillary agents.

In using the subject invention, the cytotoxic agent will be introduced into the anterior chamber of the eye following lens removal. It is preferably introduced following introduction of a non-cytotoxic agent capable of specifically binding to sites cross-reactive with the cytotoxic agent. The preferred method in carrying out the subject invention is as follows. Non-cytotoxic agent, 10–100 μg in 10–20 μl, is injected intracamerally through the limbus. For the most part, this agent will be a monoclonal antibody or a specific binding fragment thereof. Generally the solution will be a physiologically acceptable solution, which may be saline, phosphate buffered saline or the like.

Other methods of introduction can include for example instillation of the non-cytotoxic agent following incision of the cornea and instillation of about 25–200, preferably about 50–150, more preferably about 100 µl of a non-cytotoxic agent capable of specifically binding to a site cross-reactive with the cytotoxic agent.

The antibodies or fragments thereof will bind to all sites which may be cross-reactive with the cytotoxic agent and will also bind non-specifically to "hot spots" which may be present within the anterior chamber of the eye. In this way, the cells will be protected from the cytotoxic agent.

The use of the cross-reactive binding agent will be of particular importance where the cytotoxic agent has cross-reactivity, either specific or nonspecific, with cells other than lens epithelial cells. By use of the prior instillation of the cross-reactive non-cytotoxic binding moiety, cytotoxic agents may be prepared which cross-react to varying degrees with cells, particularly epithelial cells, other than lens epithelial cells.

After allowing for antibody binding (10–15 min) a corneal incision is made (see for example Extracapsular Cataract Surgery, Emery & McIntyre, Mosby Company, St. Louis, 1983) and the anterior chamber flushed with a physiologically acceptable solution such as a balanced salt solution to remove any unbound non-cytotoxic agent. Extracapsular surgery and lens removal is performed according to standard methods (Emery & McIntyre, supra). After the corneal incision is closed, a second injection is made into the lens capsule area. The material for the second injection comprises a cytotoxic composition and generally will comprise 10–20 μl containing an amount of the cytotoxic agent sufficient to substantially completely or completely kill all of the lens epithelial cells, usually about 1–10 μg.

Generally, the cytotoxic effect will be realized within a relatively short time after the instillation of the cytotoxic agents, usually in about 0.5 hrs, or shortly thereafter, when inhibition of protein synthesis may be used to evaluate onset of the cytotoxic effect. However, if viability is assessed by some other mechanism, e.g., vital stains, etc., it may be hours to days before a cytotoxic effect (e.g., cell death) is noted.

The subject compositions can be provided as kits for use in one or more operations. The kits will include the non-cytotoxic agent and the cytotoxic agent, either as concentrates, which may be further diluted prior to use or at the concentration of use, where the vials may include one or more dosages. Conveniently, single dosages may be provided in syringes, contained in sterilized containers, so that the physician may employ the syringes directly, where the syringes will have the desired amount and concentration of agents. Thus, the kit may have a plurality of syringes containing the cytotoxic agent as well as the non-cytotoxic agent in appropriate proportional amounts. Where the syringes contain the formulation for direct use, usually there will be no need for other reagents for use with the method.

The following examples are offered by way of illustration and not by way of limitation.

EXPERIMENTAL

Example 1

Preparation of Monoclonal Antibodies

A. Immunization

Mice (BALB/c) were immunized with human cervical carcinoma epithelial cells (ME180) by injecting i.p. about $5\times10^6$ cells/200 μl three times over 2 week intervals and i.v. 3 days before isolation of the spleen with $5\times10^6$ cells/200μl. Additional mice (BALB/c) were immunized with human lens epithelial cells, obtained following cataract surgery, emulsified in Freunds Complete Adjuvant. About $5\times10^5$ cell equivalents/200 μl were given per animal for the primary injection. Additional injections consisting of equivalent cell material emulsified in Freunds incomplete were given i.m. 3 weeks apart. These mice received two additional injections of either ME180 cells or human amnion cells (WISH) prior to harvesting spleens for fusion.

B. Fusion

Spleens from immunized animals were removed three to five days following the last injection and prepared as a single cell suspension. The lymphocytes then were fused with P3-X-63/Ag8.653 mouse myeloma cells under conventional conditions. See U.S. Pat. No. 4,432,751, which disclosure is incorporated herein by reference. Following fusion, the cells were resuspended in Iscoves medium containing hypoxanthine, aminopterin, and thymidine (HAT medium) and placed in wells according to the number of myeloma cells to give a density of about $10^4$ cells/well. The cells were fed on days 5, 12, and 15 by removing and replacing half of the medium. Cultures identified as positive for antibody secretion by screening assays, were transferred to 24-well plates containing 1 ml Iscoves medium containing hypoxanthine and thymidine (HT).

C. Screening (i) ME180 immunization: For screening, the hybridoma supernatant (100 μl ) and 100 μl ME180 cells ($2\times10^5$ cells/ml) were incubated at 4° for one hr and then at 37° overnight in 96-well microtiter plates. The wells were viewed microscopically to detect disturbances (disturbed adhesion). Cells showing signs of disturbance were isolated and cloned 3 times. One of the hybridomas testing positively was designated 3D4. 3D4 produces an $IgG_1$ monoclonal antibody as determined by gel diffusion using class specific antiserum (ICN).

(ii) HLE/ME180 immunization: For screening, hybridoma supernatants were tested for binding to ME180 cells by ELISA. Bound mouse immunoglobulin was detected by goat anti-mouse IgG-horse radish peroxidase. One of the hybridomas testing positively was designated 4757. This hybridoma produces an $IgG_1$, as determined by gel diffusion.

(iii) HLE/WISH immunization: For screening, hybridoma supernatant was tested for binding to WISH cells by ELISA. Bound mouse immunoglobulin was detected as described. One of the hybridomas testing positively was designated 4197-X. This hybridoma produces an $IgG_3$ antibody as determined by gel diffusion.

(iv) Human lens epithelial cell antigen: Hybridoma supernatants from fusions performed with spleen cells obtained from human lens epithelial cell immunized mice were tested by ELISA. Ninety-six well plates were coated with a Nonidet P-40 soluble fraction of human lens epithelial cells obtained following cataract surgery. Fifty microliters per well of this soluble fraction were added to 96-well plates, dried and fixed with 0.05% glutaraldehyde for 15 minutes at 25° C. The plates were washed and incubated with cell culture medium containing 10% FBS for 60 minutes at room temperature. (Kelleher, et al., *Cancer Immunol Immunother* (1983) 14:185-190 and Mujoo et al., *J. Biol. Chem.* (1986) 261:10299-10305). Hybridoma supernatants, 50 μl well, were added to the wells and incubated for 60 minutes. The wells were then washed and bound antibody detected by goat anti-mouse IgG-horse radish peroxidase. Cultures testing positive were expanded to 24 well plates and tested further for cellular binding specificity.

D. Cell Binding of Monoclonal Antibody

Supernatants from hybridomas 3D4, 4197-X and 4757 were tested by ELISA for ability to bind to both normal and tumor cells. Adherent cell lines were grown to confluence in 96-well plates and then fixed with 0.05% glutaraldehyde for 10 minutes. Suspension cultures were attached to poly L-lysine coated plates and fixed as above. Monoclonal antibody in culture medium was added to the wells and incubated at 37° C. for 1 hour. The plates were washed three time and bound mouse IgG detected with goat anti-mouse IgG conjugated to horse radish peroxidase. Binding of the monoclonal antibodies to various cell types is shown in Table 1.

TABLE 1

Binding of 3D4, 4197-X and 4757 Antibodies to Various Cell Types

| Cell line | Tissue | Cell Type | Absorbance at 450 nm* | | |
|---|---|---|---|---|---|
| | | | 3D4 | 4197-X | 4757 |
| ME180 | human cervix | epithelial | 0.40 | 0.17 | 0.28 |
| WISH | human amnion | epithelial | 0.21 | 0.16 | 0.16 |
| COLO 320 | colon | adenocarcinoma | 0.01 | 0.00 | 0.00 |
| MRC5 | human skin | fibroblast | 0.14 | 0.06 | 0.03 |
| Daudi | Burkitt lymphoid | lymphoma | 0.01 | 0.07 | 0.02 |
| Y79 | retinoblastoma | | 0.01 | 0.06 | 0.00 |
| RPMI 7932 | melanoma | melanoma | 0.03 | 0.00 | 0.00 |
| RLE | rabbit lens | epithelial | 0.70 | 0.00 | 0.43 |

*Absorbance at 450 nm: Increasing absorbance reflects increased binding of antibody to cells.

The antibodies prepared using human cervical carcinoma cells or other epithelial cells as an immunogen are capable of binding to rabbit lens epithelial cells, as well as epithelial cell lines derived from a variety of different tissues. There is little or no binding to cells of non-epithelial origin. In addition, the antibodies from 3D4, 4197-X and 4757 have been shown to bind human lens epithelial cells by immunocytochemical staining. These results are shown in Table 2.

TABLE 2

| Binding to HLE cells* | | |
|---|---|---|
| Antibody | | |
| 3D4 | 4197-X | 4757 |
| Relative staining ++ | +++ | ++ |

*Media control, or irrelevant antibodies did not stain human lens epithelial cells.

Concomitant addition of $^{125}$I-3D4 and excess unlabeled 3D4 to the cultures inhibited the binding of the labeled 3D4 by 90%. These results are shown in Table 3.

TABLE 3

| Specificity of Binding of $^{125}$I-3D4 to Epithelial Cells | | |
|---|---|---|
| | CPM $^{125}$I | |
| Addition | RLE Cells | ME180 Cells |
| $^{125}$I-3D4 in buffer control | 4480 | 2470 |

TABLE 3-continued

| Specificity of Binding of $^{125}$I-3D4 to Epithelial Cells | | |
|---|---|---|
| | CPM $^{125}$I | |
| Addition | RLE Cells | ME180 Cells |
| $^{125}$I-3D4 in excess 3D4IgG | 460 | 400 |
| % Inhibition | 90% | 84% |

EXAMPLE 2

Preparation of Toxin-A Chain-Antibody Conjugates

A. Preparation Toxin A-Chain (i) Diphtheria Toxin: Fragment A (DTA) is prepared from diphtheria toxin (Connaught Laboratories) as described (Chung and Collier, *Biochem. Biophys. Acta* (1977) 483:248–257) and is heated to 80° C. for 10 minutes to inactivate any residual traces of toxin. Enzymic activity to DTA is assayed by ADP-ribosylation of wheat germ elongation factor 2 with 14C-NAD as substrate.

(ii) Ricin Toxin: Ricin toxin was purified from castor beans (A. H. Hummert Seed Co., St. Louis, Mo.) by affinity chromatography on Sepharose 4B. (Nicolson and Blaustein, ibid. (1972) 266:543–54. Ricin toxin A-chain (RTA) was purified from whole ricin toxin by reduction from 2-mercaptoethanol and chromatography on Cellex-D (Bio-Rad) (Olsnes and Pihl, *Biochem.* (1973) 12:3121–3126). RTA is freed of residual traces of ricin toxin by repeated cycling on Sepharose 4B columns.

B. Synthesis of Toxin-SS Antibody Conjugates (i) Synthesis of (DTA)-SS antibody conjugates: Antibody 3D4 (7.0 ml, 2 mg/ml) is dialyzed against Dulbecco's phosphate buffered saline (DPBS Gibco), pH 7.4, containing antibiotic-antimycotic solution (Gibco, 5.0 ml/1). N-succinimidyl-3-(2-pyridyldithio)propionate (SPDP) (0.186 ml, 10 mM) in absolute ethanol is added to the antibody with vigorous mixing. The mixture is allowed to react for 30 min at room temperature and then dialyzed against two 1-liter changes of the same buffer. After dialysis the antibody preparation is analyzed for 2-pyridyldisulfide content as described (Stuchbury et al., *Biochem. J.* (1975) 151:417–432). DTA (3.0 ml, 2.5 mg/ml) is reduced by addition of 0.3 ml of 1.0 M dithiothreitol, pH 7.0, for 30 min at room temperature and desalted on Sephadex G-25 (2.6×12 cm column) equilibrated with the buffer described above. Peak fractions from the column are pooled (11.0 ml, 0.53 mg/ml) and mixed with PDP-(3D4) antibody (7.0 ml, 2.1 mg/ml). Final concentration of DTA and antibody are 1. 5×10–5M and 5.5×10–6M, respectively. The final molar ratio of DTA to antibody in the reaction mixture is about 3. The crude conjugate preparation (18.0 ml) is concentrated to a final volume of 0.9 ml by ultracentrifugation on an Amicon YM-10 membrane. Crude (DTA)-SS-(3D4) (9.0 ml) is chromatographed on a Sephacryl S-2000 column (2.6×10$^6$ cm, 22.1 ml/h flow rate) equilibrated with DPBS buffer. Each fraction (6.2 ml) is analyzed for ADP-ribosylation activity and by sodium dodecylsulfate/polyacrylamide gel electrophoresis (SDS/PAGE). Fractions 30–40 are pooled, concentrated on an Amicon YM-10 membrane, and are used in cytotoxicity assays after filter sterilization.

(ii) Synthesis of (RTA)-SS-(3D4) antibody conjugate: (RTA)-SS(3D4) was synthesized as described by Kernan et al. *J. Biol. Chem.* (1984) 133:137–146. Briefly, 3D4 (1 to 2 mg/ml) was dialyzed against 0.1 M NaPO$_4$, 0.1 M NaCl, pH 7.7, and 15- to 20-fold molar excess of N-succinimidyl-3-(2 pyridyldithio)propionate (SPDP) was added to the antibody with vigorous mixing. After incubation at room temperature for 30 min the pyridyl-dithiopropionate (PDP)-modified antibody solution was dialyzed against two changes of PBS. After dialysis, the PDP group to antibody ratio was determined. RTA was initially reduced by the addition of dithiothreitol at a final concentration of 50 mM, followed by incubation for 1 hour at room temperature. The RTA was then dialyzed extensively against PBS (4° C.) to remove any residual reducing agent. The RTA was then concentrated by using an Amicon stirred cell fitted with a YM10 membrane to a final concentration of 4 mg/ml. Five- or 10-fold molar excess RTA was then added to the PDP-antibody solution and incubated for 16 hrs at 4° C. The RTA-3D4 conjugate was purified by chromatography on Sephacryl S-200.

C. Effect of 3D4-Ricin A Conjugates on Target Cells:

(i) Cytotoxicity: Target cells (ME180, RPMI 7932; rabbit lens epithelial cells (RLE)) were plated in 96-well plates to achieve 25% confluence. Ricin A-conjugate (stock solution 1 mg protein/ml) or control media was added at the indicated dilutions and incubated for 10 min at either 37° or 25° C. The supernatant was removed, the cells washed twice and fresh medium without toxin conjugate added to the wells. The plates were incubated at 37° C. until control wells were confluent. Cell density then was determined by conversion of the yellow dye 3-(4,5-dimethylthiazol-2-yl)-2,5-diphenyl tetrazolium bromide (MTT) to a purple product by living cells in direct proportion to cell number and metabolic activity. Appearance of the product was measured spectrophotometrically. Mosmann, *J. Immunol. Methods* (1983) 65:55. Percent reduction in cells was calculated by:

% reduction in cells =

$$100 - \frac{\text{Cell density (absorbance) in test}}{\text{Cell density (absorbance) in control}} \times 100$$

The results are shown in Table 4, below.

TABLE 4

| 3D4-ricin A Conjugate Dilution | Cytotoxicity of 3D4-ricin A for Cells: 10 minute incubation at 37° and 25° C. Percent Reduction in Cells | | | | | |
|---|---|---|---|---|---|---|
| | Cell Type | | | | | |
| | ME180 | | RPMI 7932 | | RLE | |
| | 37° C. | 25° C. | 37° C. | 25° C. | 37° C. | 25° C. |
| 1:10 | 93 | 88 | 24 | 0 | 84 | NT* |

TABLE 4-continued

| 3D4-ricin A Conjugate Dilution | Cytotoxicity of 3D4-ricin A for Cells: 10 minute incubation at 37° and 25° C. Percent Reduction in Cells | | | | | |
|---|---|---|---|---|---|---|
| | Cell Type | | | | | |
| | ME180 | | RPMI 7932 | | RLE | |
| | 37° C. | 25° C. | 37° C. | 25° C. | 37° C. | 25° C. |
| 1:20 | 96 | 88 | 18 | 0 | 85 | |
| 1:40 | 95 | 88 | 6 | 0 | 84 | |
| 1:80 | 91 | 87 | 15 | 11 | 85 | |
| 1:160 | 81 | 74 | 9 | 11 | 83 | |
| 1:320 | 53 | 53 | 0 | 4 | 84 | |
| 1:640 | 39 | 42 | 0 | 0 | 80 | |
| 1:1280 | 24 | 10 | 2 | 0 | 70 | |
| 1:2560 | 11 | 8 | 5 | 0 | 60 | |
| 1:5120 | 1 | 0 | 15 | 0 | 59 | |

*NT - Not tested

Proliferation of specific target epithelial cells was significantly prevented by exposure to as little as 10 μg protein/ml of 3D4-ricin A conjugate, a concentration which had no effect on RPMI 7932 control cells.

(ii) Inhibition of Growth: Human lens epithelial cells obtained from cataract surgery were incubated in RPMI 1640 containing 10% FBS. For the experiment, the culture medium was removed and replaced with 3D4 RTA immunoconjugate in medium (20 μg/ml) or medium alone for 6 hours at 37° C. Following this incubation, cells were washed and given fresh culture media without conjugate and incubated for 48 hours. 3H-leucine was added to all cultures 24 hours prior to harvest of TCA precipitable protein. Thorpe et al., *Eur. J. Biochem* (1981) 116:447; Domingo and Trowbridge *Methods in Enzymology* (1985) 112:238; Vitetta et al. *Proc. Nat. Acad. Sci.USA* (1983) 80:6332. The results are shown in

TABLE 5

| Inhibition of $^3$H—leucine Incorporation by Human Lens Epithelial Cells by 3D4-ricin A | |
|---|---|
| Culture Addition | CPM Incorporated |
| 3D4-Ricin A | 3,655 |
| Medium Alone | 22,255 |

Based on these data, it appears that the monoclonal antibody-toxin conjugate is being translocated into the lens epithelial cell where the cytotoxic portion is active.

Example 3

Inhibition of Cytotoxic Effect of Conjugate by Prior Incubation With Unconjugated Monoclonal Antibody To demonstrate protection of cross-reactive cells which bind the conjugate specifically, unconjugated 3D4 or medium alone was added to the cultures 10 min. prior to 3D4-ricin toxin A conjugate addition. A dilution of conjugate (as indicated in Table 6) was then added to the cells, incubated for 60 min. at 37° C. Cells were given fresh medium and incubated for 3 days at 37° C. Cell density was determined with MTT as described above (See Example 2).

TABLE 6

| Effect of Preincubation of Cells With Unconjugated Monoclonal Antibody* | | |
|---|---|---|
| | Treatment | |
| 3D4 RTA (X 100) | 3D4 RTA | 3D4 IgG + 3D4 RTA[1] |
| 2 | 10 | 67 |
| 4 | 21 | 95 |
| 8 | 20 | 99 |

TABLE 6-continued

| Effect of Preincubation of Cells With Unconjugated Monoclonal Antibody* | | |
|---|---|---|
| | Treatment | |
| 3D4 RTA (X 100) | 3D4 RTA | 3D4 IgG + 3D4 RTA[1] |
| 16 | 32 | 98 |
| 32 | 50 | 98 |
| 64 | 60 | 98 |
| 128 | 91 | 98 |
| 256 | 87 | 98 |
| 512 | 100 | 100 |

*Expressed as a percentage of control cells not treated with conjugate.
[1]Cells were exposed to 3D4 IgG at 100 μg/ml for 10 minutes. Cells were washed 3 times and 3D4 RTA added.

Example 5

Preparation of Saporin-Antibody Conjugates

A. Isolation of Saporin

Saporin was extracted from the seeds of *Saponaria officinalis* using 0.14 M NaCl, 5 mM NaPO$_4$, pH 7.2, using 8 ml/g, by soaking the ground seeds overnight at 4° C. The supernatant was removed and centrifuged at 28,000 ×g for 30 min. The crude supernatant was dialyzed against 5 mM NaPO$_4$, pH 6.0, then purified by passage over a CM ion exchange column from which the saporin was eluted with an 0.0–0.3 NaCl gradient (linear). Fractions having ribosome-inhibiting activity were pooled and dialyzed against phosphate buffered saline (PBS) using the method of Stirpy et al., *Virchows Arch.* (1987) 53:259–271.

B. Conjugation

Purified antibody is treated with N-succinimidyl-3-(2-pyridyldithio)propionate (SPDP) for 30 min at room temperature then dialyzed against PBS to remove any unreacted SPDP groups. After dialysis the antibody preparation is analyzed for 2-pyridyldisulfide content as described in Example 2.B supra. The ratio of antibody to SPDP is 10- to 15-fold excess of SPDP to antibody. The saporin is treated with a 10-fold excess of SPDP in PBS, pH 7.0, for 30 min at room temperature then desalted on Sephadex G-25 as described in Example 2.B. Peak fractions from the column are pooled and mixed with PDP-antibody in a ratio of 5-fold molar excess of saporin to antibody. The conjugates are purified by passage over a Sephacryl-300 column. Fractions having a molecular weight in the range of about 160–210 K MW are collected and tested for immunological specificity and cytotoxicity.

Example 6

Effect of Toxin-Antibody Conjugate on Proliferation of Galago Lens Epithelial Cells in vivo Galago (bushbaby) primates are anesthetized. Prior to surgery, animals receive an injection, given intracamerally, of 10–100 μg of antibody substantially specific for lens epithelial cells in a balanced salt solution. Ten to 20 μl of antibody solution are injected through the limbus region with a 30 g needle and a microliter syringe. After allowing for antibody binding (10–15 min) a corneal incision is made (Emery et al., (1983) supra) and the anterior chamber is flushed with a balanced salt solution to remove any unbound antibody. Extracapsular surgery and lens removal are performed according to standard methods (Emery et al., (1983) supra). After the corneal incision is closed, 10–20 μl of toxin-antibody conjugate (1–10 μg) or balanced salt solution is injected into the lens capsule area. The toxin-antibody conjugate is any of the conjugates prepared (see Examples 2 and 5, supra). The animals are observed over time for development of secondary cataracts.

By introducing the subject cytotoxic agents, particularly after introduction of the non-cytotoxic binding moiety, remnant lens epithelial cells can be prevented from proliferating, thus avoiding secondary cataracts. The subject methods and compositions provide a simple procedure for preventing secondary cataracts while avoiding injury to other tissues in the eye and provide a safe alternative to the various techniques which have been used previously but which have general cytotoxic effects. By the subject two-stage treatment, a relatively non-specific cytotoxic agent (for example an antibody specific for epithelial cells) can be made specific for a certain epithelial cell population, lens epithelial cells. The unique anatomical location of the various epithelial cell types during cataract surgery renders the treatment method possible.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for inhibiting posterior lens capsule opacification after extracapsular cataract extraction, said method comprising: introducing, in conjunction with extracapsular cataract extraction, into the anterior chamber of the eye in an amount sufficient to inhibit proliferation of lens epithelial cells, a cytotoxic agent capable of binding to said epthelial cells and killing the cells without additional agents, wherein said cytotoxic agent comprises a monoclonal antibody or fragment thereof conjugated to a toxin molecule or cytotoxic moiety of a toxin molecule.

2. A method according to claim 1, wherein said cytotoxic moiety is the ricin A chain, abrin A chain, or diphtheria toxin A chain.

3. A method according to claim 1, wherein said toxin is saporin.

4. A method according to claim 1, wherein said introducing comprises injecting said cytotoxic agent into the lens capsule area.

* * * * *

UNITED STATES PATENT AND TRADEMARK OFFICE
CERTIFICATE OF CORRECTION

PATENT NO. : 4,871,350      Page 1 of 2

DATED      : October 3, 1989

INVENTOR(S): Dominic M-K. Lam et al.

It is certified that error appears in the above-identified patent and that said Letters Patent is hereby corrected as shown below:

At [56], column 1, line 2, change "Monsclonal" to --Monoclonal--.

At [56], column 2, line 5, change "Lipisones" to --Liposomes--.

At [56], column 2, line 12, change "Recin" to --Ricin--.

At [56], column 2, line 20, change "Monosclonal" to --Monoclonal--.

At column 7, line 23, change "three time" to --three times--.

At column 9, line 18, change "N-succinimidyl-3-(2 pyridyldithio) propionate" to --N-succinimidyl-3-(2-pyridyldithio) propionate--.

UNITED STATES PATENT AND TRADEMARK OFFICE
CERTIFICATE OF CORRECTION

PATENT NO. : 4,871,350

DATED : October 3, 1989

INVENTOR(S) : Dominic M-K Lam et al.

It is certified that error appears in the above-identified patent and that said Letters Patent is hereby corrected as shown below:

Column 12, Claim 1 should read as follows:

Claim 1. A method for inhibiting posterior lens capsule opacification after extracapsular cataract extraction, said method comprising:

introducing, in conjunction with extracapsular cataract extraction, into the anterior chamber of the eye in an amount sufficient to inhibit proliferation of lens epithelial cells, a cytotoxic agent capable of binding specifically to [said epthelial] any epithelial cells present in said anterior chamber and killing the cells without additional agents, wherein said cytotoxic agent comprises a monoclonal antibody or fragment thereof conjugated to a toxin molecule or cytotoxic moiety of a toxin molecule.

Signed and Sealed this

Thirtieth Day of October, 1990

Attest:

HARRY F. MANBECK, JR.

*Attesting Officer*          *Commissioner of Patents and Trademarks*